United States Patent
Alruhaimi (10) Patent No.: US 12,042,196 B1
(45) Date of Patent: Jul. 23, 2024

(54) HOLDING SCREW SYSTEM WITH STRETCHABLE INTERMAXILLARY FIXING WIRE

(71) Applicant: KING SAUD UNIVERSITY, Riyadh (SA)

(72) Inventor: Khalid Abdullah Alruhaimi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/521,568

(22) Filed: Nov. 28, 2023

(51) Int. Cl.
A61B 17/86 (2006.01)

(52) U.S. Cl.
CPC ........ *A61B 17/8635* (2013.01); *A61B 17/866* (2013.01)

(58) Field of Classification Search
CPC ............ A61B 17/8605; A61B 17/8625; A61B 17/8635; A61C 7/14; A61C 7/28; A61C 8/0096
See application file for complete search history.

(56) References Cited

U.S. PATENT DOCUMENTS

| 5,921,774 | A | 7/1999 | Kaisha |
| 7,934,927 | B2 | 5/2011 | Yazdi |
| 10,357,341 | B2 | 7/2019 | Alruhaimi |
| 10,918,463 | B1 | 2/2021 | Alruhaimi |
| 2018/0132978 | A1* | 5/2018 | Alruhaimi ............ A61C 8/0048 |

* cited by examiner

*Primary Examiner* — Olivia C Chang
(74) *Attorney, Agent, or Firm* — Nath, Goldberg & Meyer; Joshua B. Goldberg (57) ABSTRACT

A holding screw system includes a head and a shank extending from the head. The shank has an upper portion, a threaded lower portion adjacent to the upper portion defining a junction. A self-tapping tip extends from the lower portion. An annular flange is disposed at the junction between the upper portion and the threaded lower portion of the shank. The annular flange has a peripheral surface and a diameter greater than each of the head and the upper portion thereby forming a stop between the upper portion and the threaded lower portion. A bracket arm has one end extending directly from the upper portion. An open annular retainer is located at the other end of the bracket arm. The open annular retainer defines a bore and extends beyond the peripheral surface of the annular flange.

8 Claims, 7 Drawing Sheets

HOLDING SCREW SYSTEM WITH STRETCHABLE INTERMAXILLARY FIXING WIRE

BACKGROUND

1. Field

The present disclosure relates to surgical screws and fasteners used in dentistry and maxillofacial orthopedics, and particularly to a holding screw system that has a bracket arm extending from the shaft or shank of a screw for supporting a distractor or other maxillofacial fixing.

2. Description of the Related Art

Maxillofacial fractures or osteotomies typically require a strong, quick and stable fixation to maintain reduction, fixation and correct occlusion. The use of a surgical screw fastened at desired bone sites in the dental arch attached with a bracket is required to support a fixing bar or intermaxillofacial wires in order to maintain correct occlusion during reduction and fixation of maxillofacial fractures or osteotomies.

SUMMARY

A holding screw system, with open bracket rings extending from screws, eases passage and engagement of eyelets in a stretchable intermaxillary wire throughout several open ring brackets in both dental arches even if the screws are not exactly leveled during fastening. The present subject matter allows the upper and lower jaws to be fixed with the pre-made stretchable continuous eyelet wire that hangs or rests on the open bracket rings accordingly.

A holding screw system, in one embodiment, includes a head and a shank extending from the head. The shank has an upper portion and a threaded lower portion adjacent to the upper portion defining a junction. A self-tapping tip extends from the lower portion. The head and the shank define a longitudinal axis along the length of the head and the shank. An annular flange is disposed at the junction between the upper portion and the threaded lower portion of the shank. The annular flange has a peripheral surface and a diameter greater than each of the head and the upper portion thereby forming a stop between the upper portion and the threaded lower portion. A bracket arm has one end extending directly from the upper portion at an acute angle to the longitudinal axis. An open annular retainer is located at the other end of the bracket arm. The open annular retainer defines a bore. The bore has a longitudinal axis. The open annular retainer extends beyond the peripheral surface of the annular flange. The longitudinal axis of the bore extends perpendicular to the longitudinal axis of the head and shank.

The holding screw system further includes a stretchable intermaxillary wire having an eyelet. The eyelet is supported within the bore.

The stretchable intermaxillary wire includes a plurality of eyelets in some embodiments. The stretchable intermaxillary wire can be made of stainless steel or any other biocompatible material.

In some embodiments, a wire is formed in a continuous eyelet where the eyelet is supported within the bore.

The head, in one embodiment, has cruciform slots defined therein and, in other embodiments, the head is a crossed-slot head. In an alternate embodiment, the head is a Phillips head.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

The holding screw system includes a screw having a cross-slot head or a Phillips head and a shank extending from the head, the shank having a smooth upper portion, a threaded lower portion, and a self-tapping or self-drilling tip. The holding screw has an annular flange defining a stop disposed between the smooth upper portion of the shank and the threaded lower portion of the shank. The stop may have a larger diameter than the head. The screw has a bracket arm extending from the smooth upper shank at an oblique angle. The free end of the bracket arm has a round retainer, which may be circular or cylindrical and defines a smooth bore adapted for supporting a distractor or other dental appliance. The screw may be made from stainless steel or other noncorrosive, biocompatible material.

Figure 1:
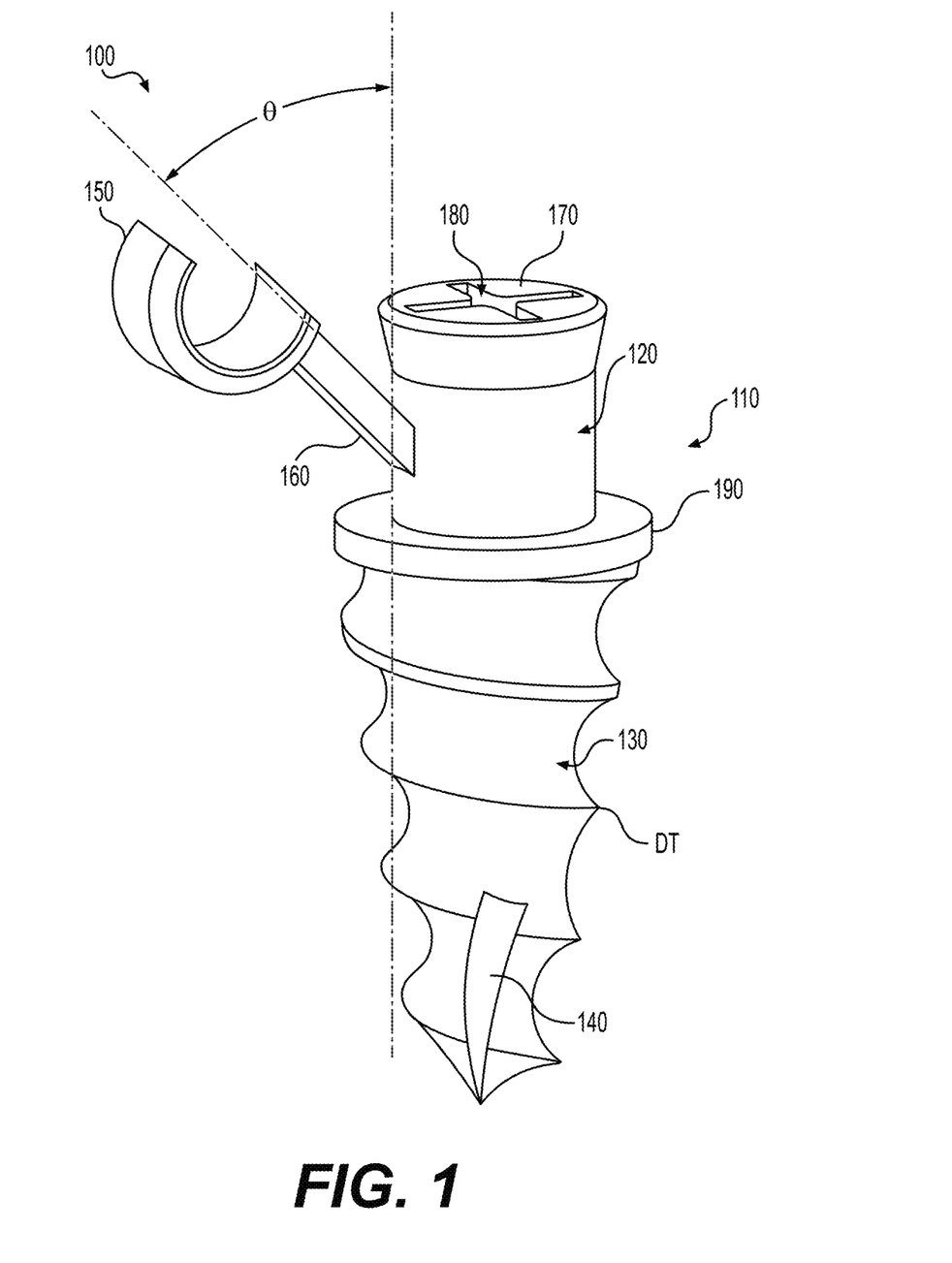
FIG. 1 is a side view of a holding screw system.
Figure 2:
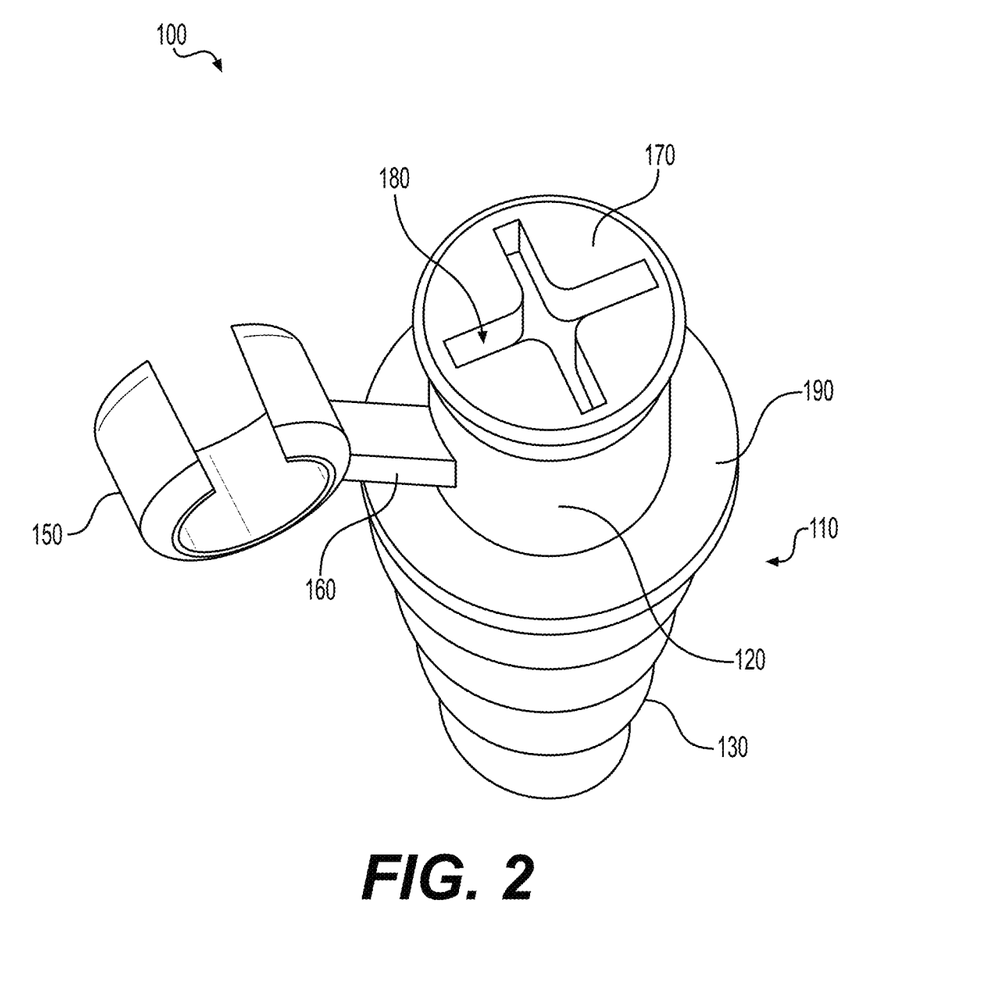
FIG. 2 is a top perspective view of the holding screw system.

As shown in FIG. 1 and FIG. 2, the holding screw 100 has a head 170 and a shank 110 extending from the head 170. The head 170 has a cruciform slot 180 defined therein. The cruciform slot 180 may be a crossed-slot head or a Phillips head. As used herein, the term "crossed-slot" head refers to two slots of substantially uniform depth that extend across substantially the entire diameter of the head 170. The crossed-slot head is designed to be used with a flat blade driver, which may alternately be inserted into one slot or the other to drive the screw, depending upon the presentation or accessibility of the head. Alternatively, the cruciform slot may be the well-known recessed cruciform slot known as a Phillips head, designed for use with a Phillips driver, which will slip from the cruciform slot 180 when the screw has been sufficiently fastened in order to avoid over-torqueing the holding screw 100.

The shank 110 has a smooth upper portion 120 and a threaded lower portion 130, the threaded lower portion being defined by a tapering inclined plane DT helically extending down the lower portion 130 of the shank 110 in conventional pattern. The lower portion 130 of the shank 110 terminates in a self-tapping or self-drilling tip 140 formed by a slot extending through the bottom two rotations of the helical thread DT, defining cutting edges. An annular flange 190 defines a stop disposed between the smooth upper portion 120 and threaded lower portion 130 of the shank 110. As best seen in FIG. 2, the stop 190 may have a greater diameter than the head 170. The annular flange acting as a stop 190 prevents the holding screw 100 from passing too deeply through the mucoperiosteum when fixing the screw to the bone.

Figure 3A:
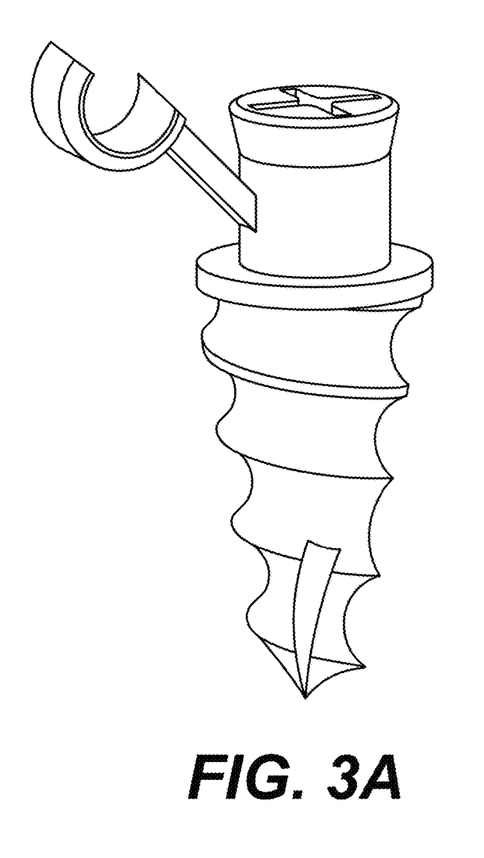
FIGS. 3A and 3B are illustration of the holding screw system with the bracket arm at different angles.
Figure 3B:
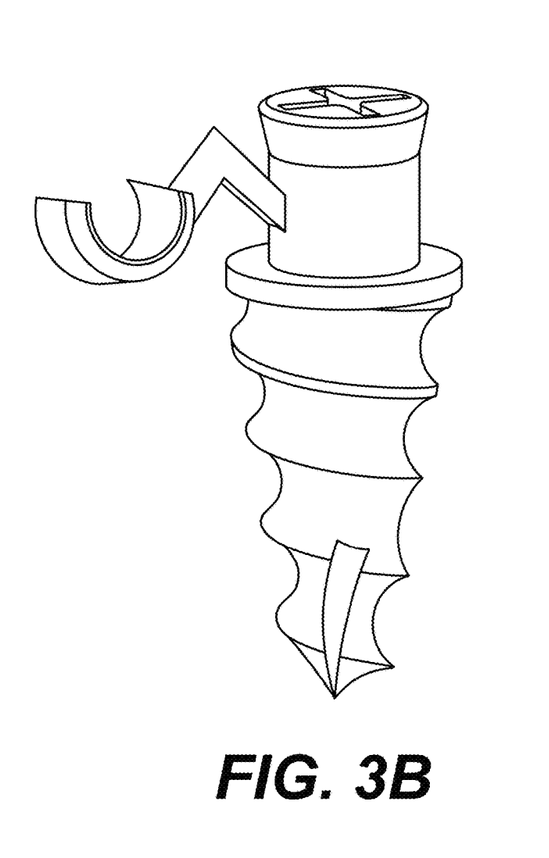

A bracket arm 160 extends from the smooth upper portion 120 of the shank 110 at an oblique angle θ. The oblique angle θ may be, e.g., about 45° (or 135°, depending upon whether the angle is measured with respect to the ascending portion of the longitudinal axis of the shank 110 or the descending portion), although oblique angles θ greater or less than 45° may be used, depending upon the application. FIG. 3A is an illustration showing the bracket arm 160 at a 450 angle and FIG. 3B is an illustration showing the bracket arm 160 with a right angle within the arm.

Figure 4:
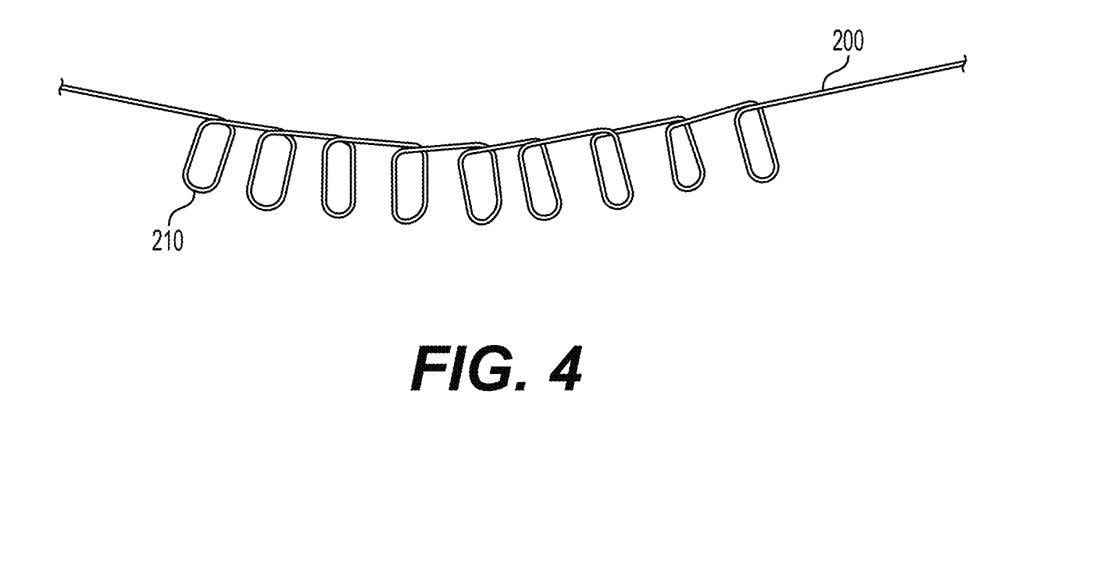
FIG. 4 is a front view of the stretchable intermaxillary wire having a plurality of eyelets in idle form.
Figure 5:
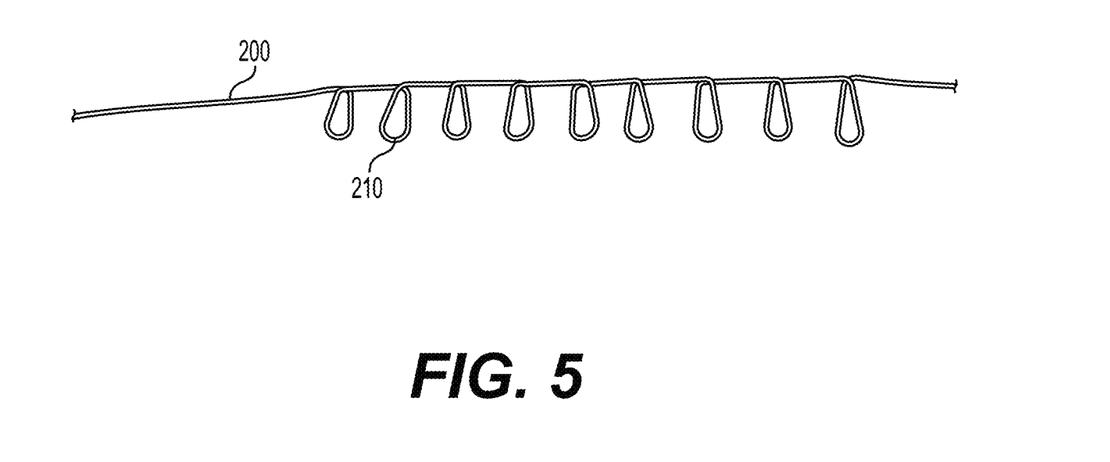
FIG. 5 is a front view of the stretchable intermaxillary wire having a plurality of eyelets in stretched form.

The bracket arm 160 terminates in an open annular retainer 150 (e.g. circular, cylindrical) that has a smooth bore for supporting a stretchable intermaxillary wire 200 having a plurality of eyelets 210 or other appliance, as shown in FIGS. 4 and 5. Since the open annular retainer 150 has an opening or break in the perimeter/circumference, it is easy to attach the eyelets 210 of the intermaxillary wire 200 onto the bore. This also allows for more random placement of the screws 100. A surgeon can fasten the screw 100 in a bone without the need of precise levelling. FIG. 4 is a front view of the stretchable intermaxillary wire 200 having a plurality of eyelets 210 in idle form and FIG. 5 is a front view of the stretchable intermaxillary wire 200 having a plurality of eyelets 210 in stretched form. The stretchable intermaxillary wire 200 is made of stainless steel or similar biocompatible material and its cross-section size is for example and not limited to 0.5 mm. The wire is formed in a continuous eyelet. It comes in several sizes (for example small, medium and large) to fit to different dental arch sizes and to be easily stretched to clutch into the open annular retainer 150 of the holding screw 100 fixed in the bone of both upper and lower arches and hold upper and lower dental arch in the correct position even if the bracket arms 160 of the bone fasteners are not fixed in a straight level.

Figure 6:
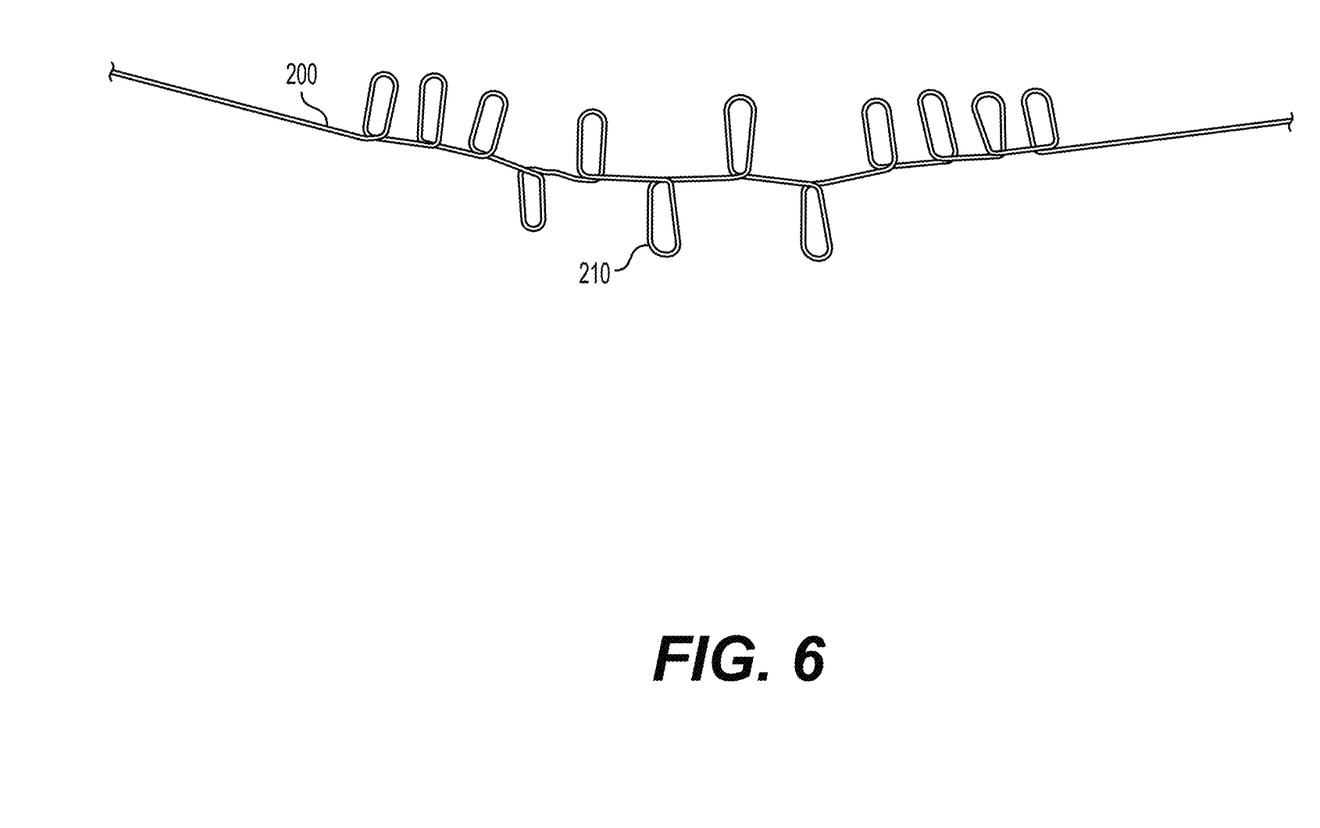
FIG. 6 is front view of the stretchable intermaxillary wire having a plurality of eyelets twisted upwards and downwards.

FIG. 6 is a front view of the stretchable intermaxillary wire 200 having a plurality of eyelets 210. The eyelets 210, as illustrated, are twisted upwards and downwards during fixation of the stretchable intermaxillary wire 200 to the dental arch with wire forceps to easily engage the open annular retainer 150 in either upper and lower dental arches. A surgeon can now fix the upper and lower arches through several opened annular brackets 150 very fast in seconds or minutes and the stretchable nature of the continuous eyelet will provide rigid fixation. The anchor load exerted by stretching the stretchable intermaxillary wire 200 is enough to clutch the stretchable intermaxillary wire 200 to the bracket arm 160 and ensures tight and stable intermaxillary fixation. Thus the plurality of wire eyelets 210 hang or rest inside the open annular retainer 150 and hold the upper and lower dental arch firmly in the desired position after reducing jaw fractures and maintains good occlusion during the healing period.

Figure 7:
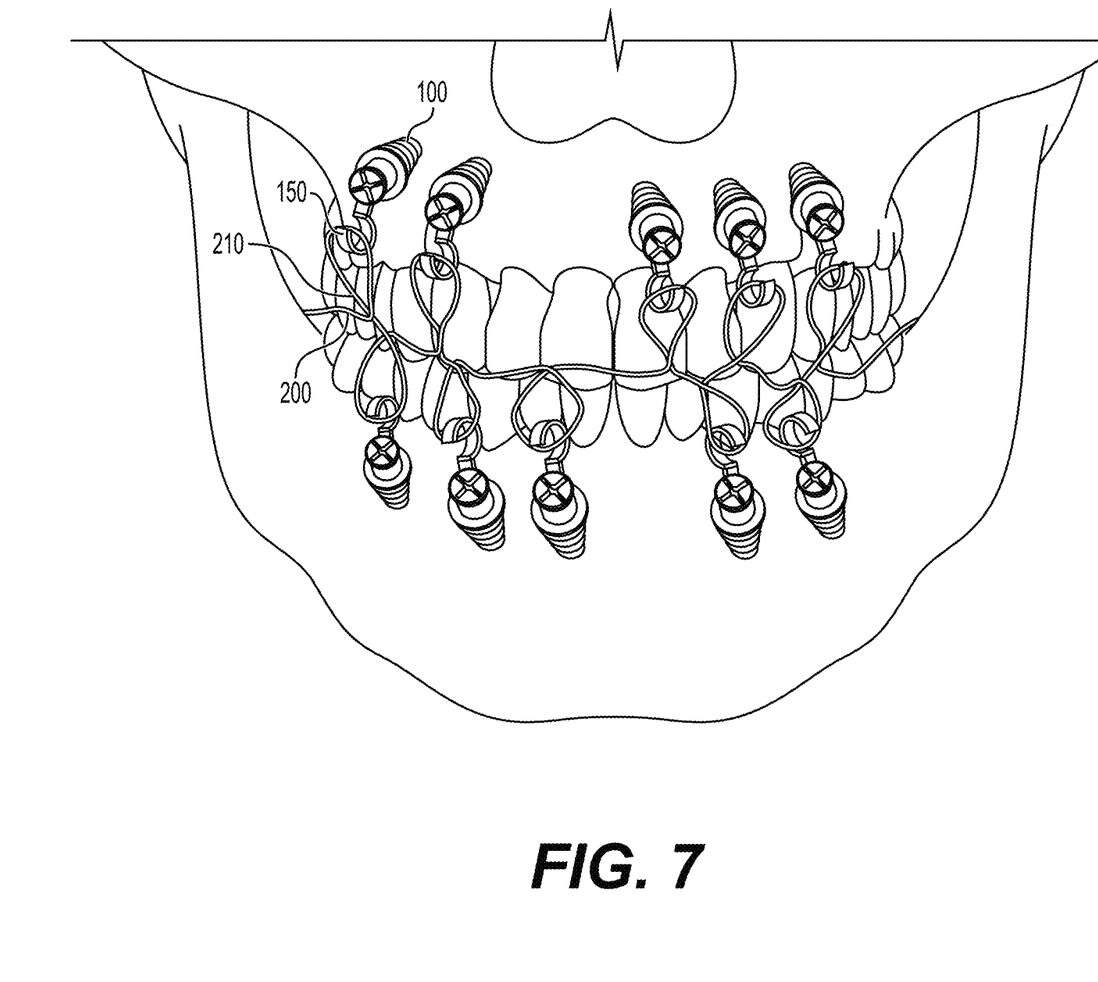
FIG. 7 is an environmental front view of the holding screw system attached to upper and lower dental arches.
Figure 8:
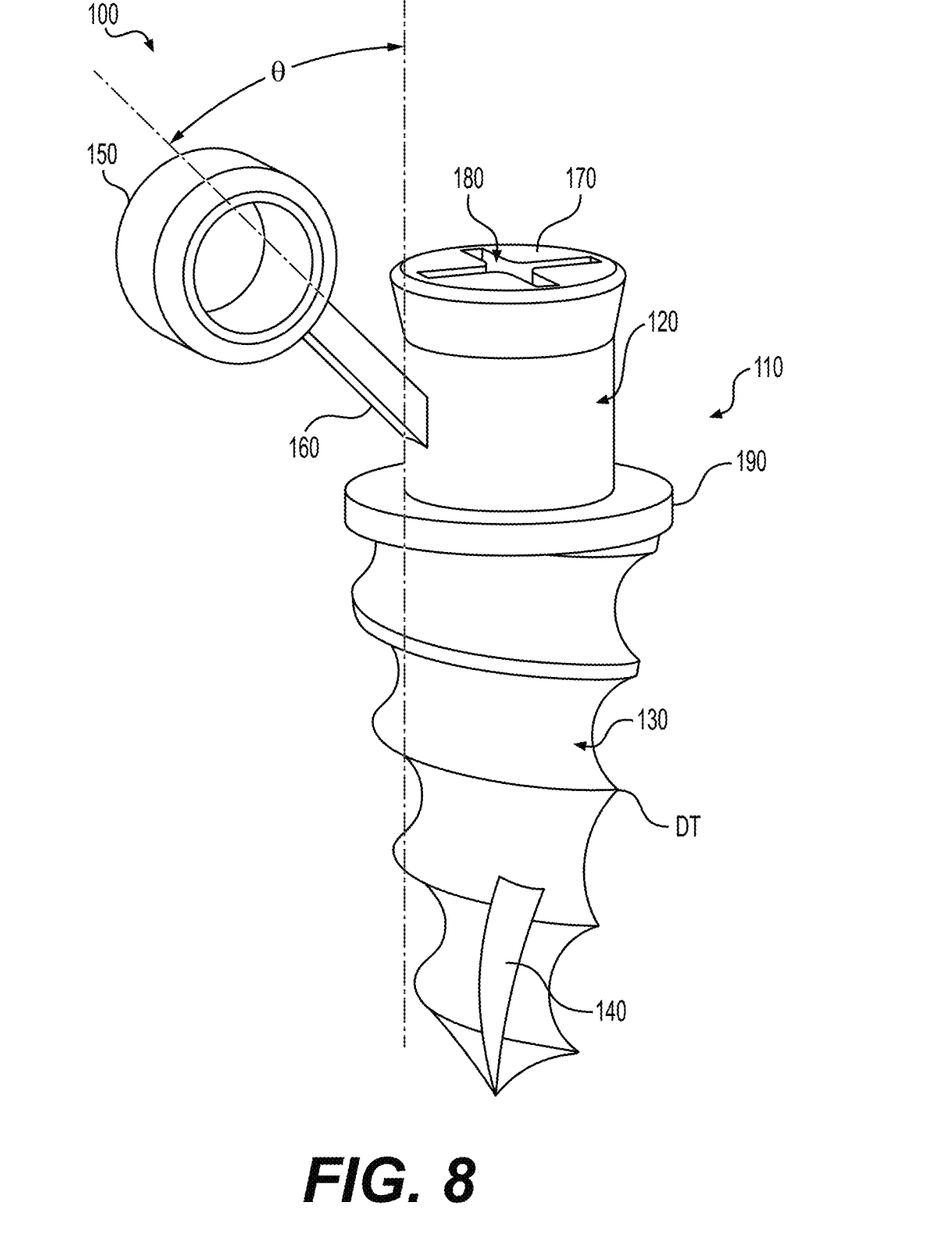

FIG. 7 is an environmental front view of the holding screw system attached to the upper and lower dental arches. The holding screws 100 are fastened in the related alveolar bone and the plurality of eyelets 210 of the stretchable intermaxillary wire 200 is engaged to several open annular retainers 150 in both jaws.

Representative dimensions of the holding screw 100 includes a length of at least 12 mm and a thickness of about 2 mm. The length of the threaded lower portion 130 of the shank 110 may be at least 6 am. The bracket arm 160 may be provided in different lengths to offset the open annular retainer 150 at different distances or heights, depending on the application. Representative lengths of the bracket arm 160 include a length approaching 0 mm, 2 mm, or 4 mm. The open annular retainer 150 may have an outer diameter of about 4 mm and a thickness of about 2 mm, defining a bore having an inner diameter of 2 mm. The stop 190 may have a diameter of 4 mm and a thickness of 1 mm. The threads of the threaded lower portion 130 of the shank 110 may have a pitch of 1 mm. It will be understood that the recitation of dimensions herein is provided for purposes of enablement, and not by way of limitation. Actual dimensions are a manufacturing detail, and may vary from the dimensions recited herein.

It is to be noted that the holding screw 100 can be used in conjunction with not only the stretchable intermaxillary wire 200 having a plurality of eyelets 210, but also with any type of distractor device, maxillofacial fixing device, or other type of dental appliance, such as for augmentation of defects resulting from cleft palate deformities, anterior congenital defects of the maxilla and the mandible, anterior jaw defects resulting from surgical removal of a cyst of pathogeneses and tumors, acquired anterior discontinuity of the maxilla or mandible defects, as well as defects due to trauma. The holding screws 100 may be fixed to the bone under local anesthesia, and provide a strong support for distraction devices and other dental appliances that can be installed and removed more quickly and easily than existing devices.

It is to be understood that the present subject matter is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A holding screw system, comprising:
    a head;
    a shank extending from the head, the shank having an upper portion, a threaded lower portion adjacent to the upper portion thereby defining a junction, and a self-tapping tip extending from the threaded lower portion to the upper portion, wherein the head and the shank define a longitudinal axis;
    an annular flange disposed at the junction between the upper portion and the threaded lower portion of the shank, the annular flange having a peripheral surface and a diameter greater than each of the head and the upper portion thereby forming a stop between the upper portion and the threaded lower portion;
    a bracket arm, the bracket arm having one end extending directly from the upper portion at an acute angle to the longitudinal axis
    an open annular retainer at the other end of the bracket arm, the open annular retainer defining a bore, the bore having a longitudinal axis, wherein the open annular retainer extends beyond the peripheral surface of the annular flange, further wherein the longitudinal axis of the bore extends perpendicular to the longitudinal axis of the head and shank; and
    a stretchable intermaxillary wire having an eyelet, the eyelet supported within the bore.

2. The holding screw system as recited in claim 1, wherein the stretchable intermaxillary wire further includes a plurality of eyelets.

3. The holding screw system as recited in claim 1, wherein the stretchable intermaxillary wire is made of stainless steel.

4. The holding screw system as recited in claim 1, wherein the stretchable intermaxillary wire is made of a biocompatible material.

5. The holding screw system as recited in claim 1, further comprising a wire formed in a continuous eyelet, the eyelet supported within the bore.

6. The holding screw system as recited in claim 1, wherein the head has cruciform slots defined therein.

7. The holding screw system as recited in claim 1, wherein the head is a crossed-slot head.

8. The holding screw system as recited in claim 1, wherein the head is a Phillips head.

\* \* \* \* \*